United States Patent

Kast et al.

Patent Number: 5,085,689
Date of Patent: Feb. 4, 1992

[54] CYCLOHEXENONE COMPOUNDS AND THEIR USE AS HERBICIDES OR PLANT GROWTH REGULATORS

[75] Inventors: Juergen Kast, Boehl-Iggelheim; Norbert Meyer, Ladenburg; Ulf Misslitz, Neustadt; Juergen Schubert, Mannheim; Johann Jung; Wilheim Rademacher, both of Limburgerhof; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 594,949

[22] Filed: Oct. 10, 1990

[30] Foreign Application Priority Data

Oct. 13, 1989 [DE] Fed. Rep. of Germany ....... 3934204

[51] Int. Cl.$^5$ .................... A01N 37/34; C07C 255/46; C07C 255/50
[52] U.S. Cl. ..................... 71/105; 558/426; 558/431; 558/414
[58] Field of Search .............. 558/426, 431; 71/105

[56] References Cited

U.S. PATENT DOCUMENTS

| | | |
|---|---|---|
| 3,950,420 | 4/1976 | Sawaki et al. .......... 71/88 X |
| 4,517,013 | 5/1989 | Becker et al. .......... 558/431 X |
| 4,744,820 | 5/1988 | Keil et al. .......... 71/123 |
| 4,780,129 | 10/1988 | Becker et al. .......... 71/123 |
| 4,898,610 | 2/1990 | Keil et al. .......... 558/426 X |
| 4,936,906 | 6/1990 | Jahn et al. .......... 71/105 |

Primary Examiner—Joseph P. Brust
Attorney, Agent, or Firm—Keil & Weinkauf

[57] ABSTRACT

Cyclohexenone compounds of the formula I

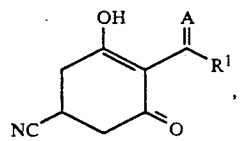

where the substituents have the following meanings:
  $R^1$ substituted or unsubstituted alkyl, alkenyl, alkynyl, cycloalkyl, phenyl or benzyl;
  A oxygen N—$OR^2$, $NR^3$;
  $R^2$ substituted or unsubstituted alkyl, alkenyl, alkynyl;
  $R^3$ hydrogen, alkyl, hydroxyalkyl, alkoxyalkyl, alkylthioalkyl, substituted or unsubstituted phenyl or benzyl;

processes for their manufacture and their use for combating unwanted plant growth and for regulating plant growth.

8 Claims, No Drawings

CYCLOHEXENONE COMPOUNDS AND THEIR USE AS HERBICIDES OR PLANT GROWTH REGULATORS

The present invention relates to cyclohexenone compounds of the formula I

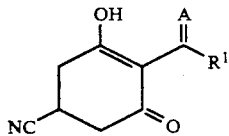

where
- $R^1$ is $C_1$–$C_{20}$-alkyl, $C_2$–$C_{20}$-alkenyl, $C_2$–$C_{20}$-alkynyl or $C_3$–$C_6$-cycloalkyl, each of which is unsubstituted or substituted by one or more halogen substituents, $C_2$–$C_6$-alkoxyalkyl, $C_2$–$C_6$-alkylthioalkyl, benzyl or phenyl, and the aromatic nuclei are each unsubstituted or monosubstituted to trisubstituted by halogen, cyano, $C_1$–$C_4$-alkyl, $C_1$–$C_4$-alkoxy, $C_1$–$C_4$-haloalkyl or nitro,
- A is oxygen, $NOR^2$ or $NR^3$,
- $R^2$ is $C_1$–$C_4$-alkyl, $C_3$- or $C_4$-alkenyl or $C_3$- or $C_4$-alkynyl, each of which is unsubstituted or substituted by one or more substituents from the group consisting of halogen, $C_1$–$C_4$-alkoxy, phenyl and hetaryl having 5 or 6 ring members and 1 or 2 hetero atoms, such as nitrogen, oxygen or sulfur, and the two last-mentioned radicals are unsubstituted or monosubstituted to trisubstituted by halogen, $C_1$–$C_4$-alkyl, $C_1$–$C_4$-alkoxy, $C_1$–$C_4$-haloalkyl or nitro,
- $R^3$ is hydrogen, $C_1$–$C_6$-alkyl, $C_1$–$C_4$-hydroxyalkyl, $C_2$–$C_4$-alkoxyalkyl, $C_2$–$C_4$-alkylthioalkyl, phenyl or benzyl, and the two last-mentioned radicals are unsubstituted or monosubstituted to trisubstituted by halogen, $C_1$–$C_4$-alkyl, $C_1$–$C_4$-alkoxy, $C_1$–$C_4$-haloalkyl or nitro, and their agriculturally useful salts and esterification products with carboxylic acids, sulfuric acids or phosphonic acids.

The present invention furthermore relates to herbicides and plant growth regulators which contain one or more cyclohexenone compounds of the formula I.

DE-A 24 39 104 discloses that cyclohexenone oxime ethers having a cyano group in the 4-position and at the same time dimethylsubstitution in the 5-position, such as 2-[1-(ethoxyamino)-ethylidene]-4-cyano-5,5-dimethylcyclohexane-1,3-dione or 2-[1-(allyloxyamino)-butylidene]-4-cyano-5,5-dimethylcyclohexane-1,3-dione, have a good herbicidal action.

DE-A 35 23 862 discloses, inter alia, cyclohexenone compounds of the structure I'

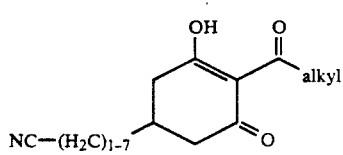

as plant growth regulators. Oxime ethers having this structure are described in DE-A 34 40 410 as herbicidal substances.

It is an object of the present invention to provide novel herbicidal and/or bioregulatory substances.

We have found that this object is achieved by the cyclohexenone compounds defined at the outset. Compounds I in which A is the radical $NOR^2$ have very good herbicidal properties, for example against species from the family of the grasses (Gramineae), while those in which A is oxygen or an imino group $NR^3$ can be advantageously used for regulating plant growth, in particular for shortening stems.

In view of the intended uses of the compounds I, preferred substituents are the following radicals:

$R^1$ is $C_1$–$C_{20}$-alkyl, in particular $C_1$–$C_6$-alkyl, such as methyl, ethyl, propyl, isopropyl, n-butyl, isobutyl, sec-butyl, tert-butyl, n-pentyl or n-hexyl, $C_2$–$C_6$-alkenyl, eg. vinyl, allyl, but-2-enyl, but-3-enyl, pent-2-enyl, pent-3-enyl, pent-4-enyl, hex-2-enyl, hex-3-enyl, hex-4-enyl or hex-5-enyl, $C_2$–$C_6$-alkynyl, eg. ethynyl, propargyl, but-2-ynyl, but-3-ynyl, pent-2-ynyl, pent-3-ynyl, pent-4-ynyl or hex-2-ynyl, $C_3$–$C_6$-cycloalkyl, such as cyclopropyl, cyclobutyl, cyclopentyl or cyclohexyl, where the stated alkyl, alkenyl, alkynyl and cycloalkyl radicals are unsubstituted or substituted by one or more, for example from 1 to 4, halogen atoms, such as fluorine, chlorine or bromine, $C_2$–$C_6$-alkoxyalkyl, eg. $C_1C_3$-alkoxy-$C_1C_4$alkyl, such as methoxymethyl, ethoxymethyl, propoxymethyl, 1-methoxyethyl, 2-methoxyethyl, 1-ethoxyethyl, 2-ethoxyethyl, 2-propoxyethyl, 1-methoxypropyl, 2-methoxypropyl, 3-methoxypropyl, 1-ethoxypropyl, 2-ethoxyp-ropyl, 3-ethoxypropyl, 1-methoxybutyl, 2-methoxybutyl, 3-methoxybutyl, 4-methoxy-butyl, 1-ethoxybutyl, 2-ethoxybutyl, 3-ethoxybutyl or 4-ethoxybutyl, $C_2$–$C_6$-alkylthioalkyl, eg. methylthiomethyl, ethylthiomethyl, propylthiomethyl, methylthioethyl, ethylthioethyl, propylthioethyl, methylthiopropyl or ethylthiopropyl, benzyl or phenyl, where the aromatic nuclei are unsubstituted or monosubstituted to trisubstituted by halogen, such as chlorine, bromine or fluorine, cyano, nitro, $C_1$–$C_4$-alkyl, such as methyl, ethyl, propyl or butyl, $C_1$–$C_4$-alkoxy, such as methoxy, ethoxy, propoxy or butoxy, $C_1$–$C_4$-haloalkyl, such as trifluoromethyl, difluorochloromethyl, difluoromethyl, trichloromethyl, pentafluoroethyl, tetrafluoroethyl, fluoropropyl, fluorobutyl, chloropropyl or chlorobutyl, $R^2$ is unsubstituted or monosubstituted or polysubstituted, eg. monosubstituted to trisubstituted, $C_1$–$C_4$-alkyl, such as methyl, ethyl, propyl, isopropyl, n-butyl, isobutyl, sec-butyl or tert-butyl, unsubstituted or monosubstituted to trisubstituted $C_3$- or $C_4$-alkenyl, such as allyl, but-2-enyl or but-3-enyl, or unsubstituted or monosubstituted $C_3$- or $C_4$-alkynyl, such as propargyl, but-2-ynyl or but-3-ynyl.

Suitable substituents are:
halogen, such as fluorine, chlorine or bromine, $C_1$–$C_4$-alkoxy as stated for $R^1$,
phenyl or hetaryl having 5 or 6 ring members and 1 or 2 hetero atoms, such as nitrogen, oxygen or sulfur, eg. pyrazolyl, imidazolyl, isoxazolyl, oxazolyl, isothiazol-yl, thioxazolyl, pyridyl, pyrimidyl, furyl, thienyl or pyrrolyl, phenyl and thienyl being preferred. The stated aromatic radicals may be monosubstituted to trisubstituted by halogen, $C_1$–$C_4$- alkyl, $C_1$-$C_4$-alkoxy or $C_1$-$C_4$-haloalkyl. Examples are phenyl, methylphenyl, ethylphenyl, propylphenyl, butylphenyl, methoxyphenyl, ethoxyphenyl, propoxyphenyl, butoxyphenyl, 3,4-dichlorophenyl, 2,6-dichlorophenyl, 4-chlorophenyl, 4-bromophenyl, 2-bromophenyl, 3-trifluoromethylphenyl, thien-2-yl, 5-chlorothienyl, 5-chlorothien-2-yl-, 4-bromothien-2-yl, thien-3-yl, 5-chlorothien-3-yl, 4,5-dichlorothien-3-yl, 5-bromothien-3-yl, 2,5-dichlorothien-3-yl, isoxazolidin-5-yl, oxazolyl, isoxazolinyl, thiazolyl, thiazolinyl, thiazolidinyl, 3-methylisoxazol-5-yl, 3-methoxymethylisoxazol-5-yl, 3-phenylisoxazol-5-yl and 5-isopropyl-1,3,4-oxadiazol-2-yl.

$R^3$ is hydrogen, $C_1$-$C_6$-alkyl as stated for $R^1$, $C_1$-$C_4$-hydroxyalkyl, such as 2-hydroxyethyl, 2-hydroxypropyl, 2-hydroxybutyl, 3-hydroxypropyl or 3-hydroxybutyl, $C_1$-$C_4$-alkoxyalkyl, such as 2-methoxyethyl, 2-ethoxyethyl, 2-methoxypropyl or 3-methoxypropyl, $C_1$-$C_4$-alkylthioalkyl, such as 2-methylthioethyl, 2-ethylthioethyl, 2-methylthiopropyl or 3-methylthiopropyl, or phenyl or benzyl, where the aromatic radicals may be monosubstituted to trisubstituted by halogen, $C_1$-$C_4$-alkyl, $C_1$-$C_4$-haloalkyl or nitro, specifically as stated in the case of $R^1$.

In formula I, $R^1$ is particularly preferably methyl, ethyl, n-propyl, isopropyl, n-butyl, isobutyl, sec-butyl, tert-butyl, n-pentyl, cyclopropyl, cyclobutyl, cyclopentyl or cyclohexyl;

where A is $NOR^2$, $R^2$ is particularly preferably ethyl, propyl, allyl, (E)-but-2-en-1-yl, propargyl, but-2-yn-1-yl, 2-fluoroethyl-, (E)-3-chloroprop-2-en-1-yl, 4-phenylbut-2-en-1-yl, 4-(4-fluorophenyl)-but-2-en-1-yl, 4-(4-chlorophenyl)-but-2-en-1-yl, 4-(4-fluorophenyl)-but-3-en-1-yl, 4-(4-chlorophenyl)-but-3-en-1-yl or 5-chlorothenyl, and where A is $NR^3$, $R^3$ is particularly preferably hydrogen, methyl, ethyl, n-propyl, isopropyl, n-butyl, sec-butyl, tert-butyl, n-pentyl, n-hexyl, allyl, hydroxyethyl, 2-methoxyethyl, benzyl or phenyl.

Among the stated preferred substituents, the following radicals are very particularly preferred:

$R^1$ is methyl, ethyl, n-propyl, n-butyl or cyclopropyl, $R^2$ (A=$NOR^2$) is ethyl, allyl, (E)-but-2-en-1-yl, propargyl, but-2-yn-1-yl, (E)-3-chloroprop-2-en-1-yl, 4-(4-fluorophenyl)-but-2-en-1-yl, 4-(4-chlorophenyl)-but-2-en-1-yl, 4-(4-fluorophenyl)-but-3-en-1-yl, 4-(4-chlorophenyl)-but-3-en-1-yl or 5-chlorothenyl, and $R^3$ (A=$NR^3$) is hydrogen, methyl, ethyl, n-propyl, isopropyl, n-butyl, sec-butyl, isobutyl, n-hexyl, allyl, 2-methoxyethyl, benzyl or phenyl.

Suitable salts of the compounds of the formula I are agriculturally useful salts, for example alkali metal salts, in particular the sodium or potassium salt, alkaline earth metal salts, in particular the calcium, magnesium or barium salt and manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Examples of suitable esterification products are esters with low molecular weight carboxylic acids, for example $C_1$-$C_6$-carboxylic acids, such as acetic esters, propionic esters, benzoic esters or benzenesulfonic esters.

The compounds I where A is $NOR^2$ or $NR^3$ can advantageously be prepared via the key intermediate Ia (compound I in which A is oxygen).

The compound Ia is prepared, according to the invention, by reacting the corresponding formyl-substituted cyclohexenone compound II

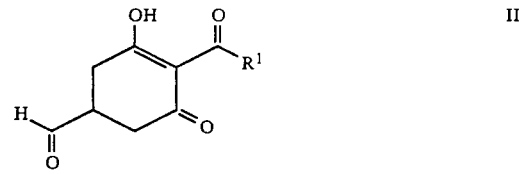

with hydroxylamine-O-sulfonic acid in an inert solvent at from 0 to 150° C.

It has proven particularly advantageous to carry out the reaction in water with from 1 to 100 parts by weight, based on starting material II, of water, at a pH of from 1 to 9 and at from 20 to 80° C, in particular from 20 to 40° C.

The reaction route is shown in the following scheme:

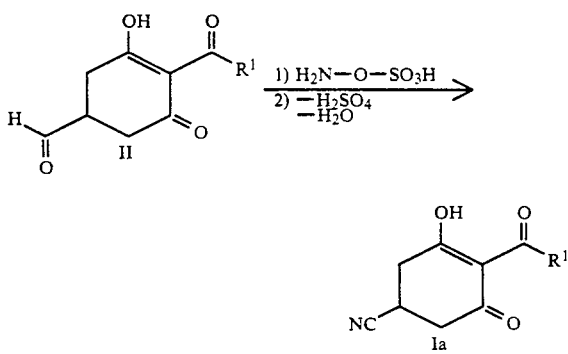

The formyl compound II is obtainable as described in EP-A 233 568.

The reaction can be carried out in the homogeneous or heterogeneous aqueous phase, with or without the addition of a buffer. For this purpose, the formyl compound II is suspended in water or is dissolved by adding a water-miscible organic solvent, eg. methanol or ethanol. It is also possible to dissolve the formyl compound II in water-immiscible solvents, such as ethers, eg. diethyl ether or tetrahydrofuran, chlorohydrocarbons, such as methylene chloride, chloroform or dichloroethane, esters, such as ethyl acetate or aromatic compounds, such as benzene, toluene or xylenes. The hydroxylamine-O-sulfonic acid, in solid form or as an aqueous solution, is added to the mixture of the solvent and the starting material II.

If the reaction is carried out in the heterogeneous phase, it is advantageous to ensure thorough mixing of the phases.

In order to achieve complete conversion to the cyano compound, it is advisable to use the reactants in equimolar amounts. For reasons relating to process engineering, it may be advisable to use the formyl compound II or the hydroxylamine-0-sulfonic acid in an excess of, for example, from 1 to 100 mol %. The hydroxylamine-0-sulfonic acid is preferably used in an excess of from 10 to 20 mol %.

In some cases, it may be useful to accelerate the reaction by adding a base. For example, from 0 to 3 equivalents, based on II, of the base may be added.

Examples of suitable bases are alkali metal hydroxides, such as NaOH or KOH, ammoniumhydroxide, alkaline earth metal hydroxides, such as magnesium hydroxide or calcium hydroxide, alkali metal carbonates and alkali metal bicarbonates.

The reaction can be carried out under atmospheric, superatmospheric or reduced pressure, continuously or batchwise, by the conventional methods.

The cyanocyclohexenone compound Ia can be isolated from, the crude reaction mixture in a conventional manner, for example by extraction or filtration.

In addition to the novel process, the cyclohexenone compounds Ia can also be prepared by reacting II with hydroxylamine and then eliminating water. Furthermore, the compounds Ia can be prepared by the conventional methods, starting from the corresponding carboxylic acids or derivatives thereof or the corresponding halogen compounds (cf. Houben-Weyl Vol. E5/II, page 1318 et seq.).

Cyclohexenone compounds of the general formula I where A is $N-OR^2$ and $R^1$ and $R^2$ have the above-mentioned meanings can be prepared in a known manner from the compounds Ia.

For this purpose, the latter are reacted with a corresponding hydroxylamine $$H_2N-OR^2 \quad III$$

or advantageously with the ammonium salt of III in the presence of a base.

The reaction is advantageously carried out in the heterogeneous phase in a solvent at an adequate temperature below about 80° C or at the boiling point of the reaction mixture.

Examples of suitable bases are carbonates, bicarbonates, acetates, alcoholates, hydroxides or oxides of alkali metals or alkaline earth metals, in particular sodium hydroxide, potassium hydroxide, magnesium oxide or calcium oxide. Organic bases, such as pyridine or tertiary amines, may also be used. The base is added, for example, in an amount of from 0.5 to 2 moles, based on the ammonium compound (cf. DE-A 34 33 767).

Examples of suitable solvents are dimethyl sulfoxide, alcohols, such as methanol, ethanol or isopropanol, aromatic hydrocarbons, such as benzene or toluene, chlorohydrocarbons, such as chloroform or dichloroethane, aliphatic hydrocarbons, such as hexane or cyclohexane, esters, such as ethyl acetate, and ethers, such as dioxane or tetrahydrofuran.

The reaction is complete after a few hours and the desired product can be isolated, for example, by evaporating down the mixture, partitioning the residue between methylene chloride and water and distilling off the solvent under reduced pressure.

When the free hydroxylamine base III is used, for example in the form of an aqueous solution, a single-phase or two-phase reaction mixture is obtained, depending on the solvent used for the starting material Ia.

Suitable solvents for this reaction are, for example, methanol, ethanol, isopropanol, aromatic hydrocarbons, such as benzene or toluene, chlorohydrocarbons, such as chloroform or dichloroethane, aliphatic hydrocarbons, such as hexane or cyclohexane, esters, such as ethyl acetate, ethers, such as dioxane or tetrahydrofuran, and nitriles, such as acetonitrile.

Alkali metal salts of the compounds I where A is oxygen or $N-OR^2$ can be obtained by treating the 3-hydroxy compounds with sodium hydroxide, potassium hydroxide, a sodium alcoholate or a potassium alcoholate in aqueous solution or in an organic solvent, such as methanol, ethanol, acetone or toluene.

Other metal salts, for example manganese, copper, zinc, iron, calcium, magnesium and barium salts, can be prepared from the sodium salts in a conventional manner, and ammonium, phosphonium, sulfonium or sulfoxonium salts can be prepared using ammonia or phosphonium, sulfonium or sulfoxonium hydroxides. The esters can be prepared by reacting a compound of the formula I with an acyl chloride in the presence of a base (eg. triethylamine) in an inert solvent by the conventional methods.

Cyclohexenone compounds of the general formula I where A is $NR^3$ and $R^1$ and $R^3$ have the abovementioned meanings can be prepared in a known manner from the compounds of the general formula Ia.

For this purpose, the cyclohexenone compound is reacted with an amine $H_2NR^3$. The reaction is advantageously carried out in the homogeneous phase in a solvent at an adequate temperature below about 80° C. or at the boiling point of the reaction mixture. Examples of suitable solvents are dimethyl sulfoxide, alcohols, such as methanol, ethanol or isopropanol, aromatic hydrocarbons, such as benzene or toluene, chlorohydrocarbons, such as chloroform or dichloroethane, aliphatic hydrocarbons, such as hexane or cyclohexane, esters, such as ethyl acetate, and ethers, such as dioxane or tetrahydrofuran.

The reaction is complete after a few hours and the desired product can be isolated by evaporating down the mixture, partitioning the residue between methylene chloride and water and distilling off the solvent under reduced pressure.

The Examples which follow illustrate the preparation of the novel cyclohexenone compounds I. Preparation Methods

EXAMPLE 1.1

3,5-Dioxo-4-acety-lcyclohexanenitrile 19.3 g (0.11 mol) of 5-formyl-2-acetylcyclohexane-1,3-dione in 200 ml of distilled water were initially taken, and 14.7 g (0.13 mol) of hydroxylamine-O-sulfonic acid were added at room temperature. The mixture was then stirred for 17 hours at room temperature. The precipitate was filtered off under suction, washed with water and dried. 11.5 g (61% of theory) of 3,5-dioxo-4-acetylcyclohexanenitrile of melting point 66–69° C. were obtained.

EXAMPLE 1.2

3,5-Dioxo-4-propionylcyclohexanenitrile 30.7 g (0.16 mol) of 5-formyl-2-propionylcyclohexane-1,3-dione in 150 ml of distilled water were initially taken, and 21.0 g (0.19 mol) of hydroxylamine-O-sulfonic acid were added at room temperature. Stirring was then carried out overnight at room temperature. The precipitate was filtered off under suction, washed with water and dried. 23.8 g (71% of theory) of 3,5-dioxo-4-propionylcyclohexanenitrile of melting point 70–74° C. were obtained.

EXAMPLE 1.5

3,5-Dioxo-4-palmitoylcyclohexanenitrile 43 g (0.12 mol) of 5-formyl-2-palmitoylcyclo-hexane-1,3-dione were suspended in 150 ml of distilled water. 15.7 g (0.14 mol) of hydroxylamine-O-sulfonic acid, dissolved in 50 ml of water, were added. The heterogeneous reaction mixture was stirred overnight at room temperature. The solid obtained was filtered off under suction, washed with water and dried. 37.7 g (86% of theory) of 3,5-dioxo-4-palmitoylcyclohexanenitrile of melting point 66–69° C. were isolated.

The cyclohexenone compounds Ia shown in Table 1 can be prepared in a similar manner.

TABLE 1

Cyclohexenone compounds Ia

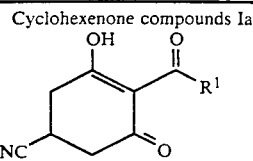

Ia

| No. | R$^1$ | Physical data mp. [°C.], $^1$H-NMR (CDCl$_3$, δ in ppm) |
|---|---|---|
| 1.1 | Methyl | 94 to 97 |
| 1.2 | Ethyl | 70 to 74 |
| 1.3 | Propyl | 47 to 50 |
| 1.4 | Butyl | 58 to 59 |
| 1.5 | Pentadecanyl | 66 to 69 |
| 1.6 | Cyclopropyl | 1.2(m, 2H); 1.35(m, 2H); 3.0(m, 2H); 3.3(m, 1H); 3.55(m, 1H) |
| 1.7 | Cyclohexyl | |
| 1.8 | Phenyl | |
| 1.9 | 4-Chloro-4-nitrophenyl | 184–187 (decomposition) |

EXAMPLE 2.3

Preparation Example for oxime ethers 3.1 g (0.016 mol) of 3,5-dioxo-4-propionylcyclohexanenitrile were dissolved in 50 ml of dry methanol, and 2.2 g (0.018 mol) of but-2-enyloxyamine hydrochloride and 1.5 g (0.018 mol) of sodium bicarbonate were added in succession. The reaction mixture was then stirred for 16 hours at room temperature. It was worked up by stripping off the solvent under reduced pressure and chromatographing the residue over silica gel using 98 : 2 methylene chloride/methanol. 2.2 g (52% of theory) of 3,5-dioxo-4-1-(but-2-enyloximino)-propyl]-cyclohexanenitrile were isolated.

The compounds Ib shown in Table 2 can be prepared similarly.

TABLE 2

Cyclohexenone compounds Ib

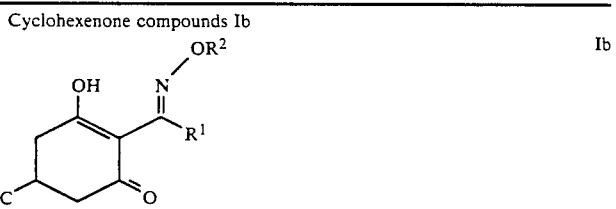

Ib

| No. | R$^1$ | R$^2$ | phys. data ($^1$H-NMR in CDCl$_3$, δ ppm) |
|---|---|---|---|
| 2.1 | Ethyl | Ethyl | 1.17(t, 3H); 1.34(t, 3H); 2.98(q, 2H); 3.15–3.33(m, 1H); 4.13(q, 2H); |
| 2.2 | Ethyl | Allyl | 1.14(t, 3H); 2.7–2.88(m, 4H); 2.96(q, 2H); 3.15–3.35(m, 1H); 4.56(d, 2H); |
| 2.3 | Ethyl | (E)-But-2-enyl | |
| 2.4 | Ethyl | (E)-3-chloroprop-2-enyl | |
| 2.5 | Ethyl | (E)-4-(4-fluorophenyl)-but-2-enyl | 1.15(t, 3H); 2.78(m, 4H); 2.95(q, 2H); 3.22(m, 1H); 3.41(d, 2H); 4.5(d, 2H); |
| 2.6 | Ethyl | 5-chlorothenyl | |
| 2.7 | Methyl | (E)-3-chloroprop-2-enyl | 2.35(s, 3H); 3.26(m, 1H); 4,54(d, 2H); 6.12(m, 1H); 6.38(d, 1H); |
| 2.8 | Methyl | (E)-But-2-enyl | 1.79(d, 3H); 2.47(s, 3H); 3.24(m, 1H); 4.48(d, 2H); 5.68(m, 1H); 5.9(m, 1H); |
| 2.9 | Propyl | Ethyl | 1.01(t, 3H); 1.35(t, 3H); 1.58(dt, 2H); 2.97(t, 2H); 3.25(m, 1H); 4.15(q, 2H); |
| 2.10 | Propyl | Allyl | 0.99(t, 3H); 1.58(dt, 2H); 2.93(t, 2H); 3.24(m, 1H); 4.46(d, 2H); |
| 2.11 | Propyl | (E)-3-chloroprop-2-enyl | 0,97(t, 3H); 1.55(dt, 2H); 2.9(t, 2H); 3.26(m, 1H); 4.45(d, 2H); |
| 2.12 | Propyl | (E)-But-2-enyl | 0,96(t. 3H); 1.59(dt, 2H); 1.79(d, 3H); 2.94(t, 2H); 3.22(m, 1H); 4.47(d, 2H); |
| 2.13 | Propyl | 5-chlorothenyl | 0,97(t, 3H); 1.54(dt, 2H); 2.86(t, 2H); 3.23(m, 1H); 5.1(s, 2H); 6.84(d, 1H); |
| 2.14 | Pentadecanyl | Ethyl | 0,88(t, 3H); 1.26(m, 31H); 2.8(m, 4H); 2.97(d, 2H); 3.23(m, 1H); 4.13(q, 2H); |
| 2.15 | Pentadecanyl | Allyl | 0,87(t, 3H); 1.26(m, 31H); 2.6–3.0(m, 6H); 3.23(m, 1H); 4.55(d, 2H); |
| 2.16 | Pentadecanyl | (E)-But-2-enyl | 0,88(t, 3H); 1.27(m, 31H); 1.8(d, 3H); 2.8(m, 4H); 2.96(t, 2H); 3.22(m, 1H); |
| 2.17 | Pentadecanyl | (E)-3-chloroprop-2-enyl | 0,87(t, 3H); 1.25(m, 31H); 2.88(m, 6H); 3.25(m, 1H); 4.54(d, 2H); 6.12(m, 1H); |

TABLE 2-continued

Cyclohexenone compounds Ib

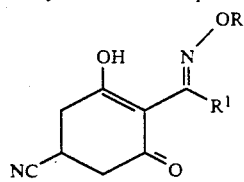

| No. | R¹ | R² | phys. data (¹H-NMR in CDCl₃, δ ppm) |
|---|---|---|---|
| 2.18 | Pentadecanyl | Propargyl | 0,9(t, 3H); 1.24(m, 28H); 2.58(t, 1H); 2.9(m, 6H); 4.66(d, 2H); |
| 2.19 | Pentadecanyl | (E)-4-(4-fluorophenyl)-but-2-enyl | 0,89(t, 3H); 1.26(m, 28H); 1.8(d, 3H); 2.8(m, 4H); 2.94(t, 2H); 3.22(m, 1H); |
| 2.20 | Pentadecanyl | 5-chlorothenyl | 0,88(t, 3H); 1.24(m, 28H); 2.84(m, 6H); 3.21(m, 1H); 5.1(s, 2H); 6.85(m, 2H); |
| 2.21 | Butyl | Ethyl | |
| 2.22 | Methyl | Ethyl | 1,35(t, 3H); 3,45(s, 3H); 3,0(m, 1H); 4,15(q, 2H); |
| 2.23 | Methyl | 5-chlorothenyl | 2,35(s, 3H); 3,25(m, 1H); 5,1(s, 2H); 6,85(d, 1H); 6,9(d, 1H); |
| 2.24 | 4-chloro-2-nitro-phenyl | Ethyl | 0,85 u. 1,4(t, 3H); 7,1 u. 7,25(d, H); 7,6 u. 7,7(dd, 1H); 8,15(d, 1H); |
| 2.25 | 4-chloro-2-nitro-phenyl | Allyl | 7,15 u. 7,25(d, 1H); 7,6 u. 7,65(d, 1H); 8,1(s, 1H); |

EXAMPLE 3.3

1.2 g (0.006 mol) of 3,5-dioxo-4-propionylcyclohexanenitrile were dissolved in 40 ml of dry tetrahydrofuran, and 0.4 g (0.006 mol) of isopropylamine was added. The mixture was stirred for 16 hours at room temperature, the solvent was stripped off under reduced pressure and the residue was filtered under suction over a little silica gel using methylene chloride/methanol. The solvent was stripped off to give 1.3 g ($\hat{=}$ 92% of theory) of 3,5-dioxo-4-(1-isopropyliminopropyl)-cyclohexanenitrile.

The cyclohexenone compounds Ic shown in Table 3 can be prepared similarly.

TABLE 3

Cyclohexenone compounds Ic

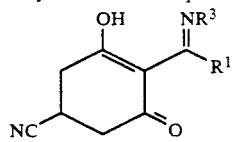

| No. | R¹ | R³ | phys. data (¹H-NMR in CDCl₃, δ ppm) |
|---|---|---|---|
| 3.1 | Ethyl | Isobutyl | 1.06(d, 6H); 1.21(t, 3H); 1.99(m, 1H); 3.0(q, 2H); 3.2(m, 1H); 3.2(t, 2H); |
| 3.2 | Ethyl | s-Butyl | 0.98(t, 3H); 1.21(t, 3H); 1.3(d, 3H); 3.19(m, 1H); 3.8(m, 1H); |
| 3.3 | Ethyl | i-Propyl | 1.22(t, 3H); 1.35(d, 6H); 3.2(q, 2H); 3.19(m, 1H); 4.03(m, 1H); |
| 3.4 | Ethyl | Benzyl | 1.2(t, 3H); 3.08(q, 2H); 3.2(m, 1H); 4.69(d, 2H); 7.35(m, 5H); |
| 3.5 | Methyl | Isobutyl | 1,05(d, 6H); 2,0(m, 1H); 2,55(s, 3H); 2,75(m, 4H); |
| 3.6 | Cyclopropyl | Isopropyl | 1,3(m, 10H); 2,85(m, 4H); |
| 3.7 | Cyclopropyl | Isobutyl | 1,3(m, 10H); 2,85(m, 4H); 3,35(m, 1H); |

The herbicidal compounds Ib, and growth-regulating agents Ia and Ic according to the invention may be applied for instance in the form of directly sprayable solutions, powders, suspensions including high-percentage aqueous, oily or other suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are generally suitable for the preparation of solutions, emulsions, pastes and oil dispersions to be sprayed direct. Examples of inert additives are mineral oil fractions of medium to high boiling Point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives methanol, ethanol, propanol, butanol, cyclohexanol, cyclohexenone, chlorobenzene, isophorone, etc.. and strongly polar solvents such as N,N-dimethylformamide, dimethyl sulfoxide, 20 N-methyl-pyrrolidone and water.

Aqueous formulations may be prepared from emulsion concentrates, pastes. oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent emulsifying or dispersing Examples of surfactants are: alkali metal, alkaline earth metal and ammonium salts of aromatic sulfonic acids. e.g.. ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, hexadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels. silicates, talc, kaolin, attapulgus clay, limestone, lime chalk, bole, loess, clay, dolomite, diatomaceous earth, calcium sulfate, magnesium sulfate, magnesium oxide, ground plastics, fertilizers such as ammonium sulfate, ammonium phosphate ammonium nitrate and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % according to the NMR spectrum).

The compounds I according to the invention may be formulated for example as follows:

I. 90 parts by weight of compound no. 1.1 is mixed with 10 parts by weight of N-methyl-alpha-pyrrolidone. A mixture is obtained which is suitable for application in the form of very fine drops.

II. 20 parts by weight of compound no. 1.3 is dissolved in a mixture consisting of 80 parts by weight of xylene. 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and I mole of castor oil. By pouring the solution into 100,000 parts by weight of water and uniformly distributing it therein an aqueous dispersion is obtained containing 0.02% by weight of the active ingredient.

III. 20 parts by weight of compound no. 1.3 is dissolved in a mixture consisting of 40 parts by weight of cyclohexenone, 30 parts by weight of isobutanol, 20 parts by weight of the adduct of 7 moles of ethylene oxide and 1 mole of isooctylphenol, and 10 parts by weight of the adduct of 40 moles of ethylene oxide and I mole of castor oil. By pouring the solution into 100,000 parts by weight of water and finely distributing it therein, an aqueous dispersion is obtained containing 0.02% by weight of the active ingredient.

IV. 20 parts by weight of compound no. 1.5 is dissolved in a mixture consisting of 25 parts by weight of cyclohexenone, 65 parts by weight of a mineral oil fraction having a boiling point between 210 and 280° C. and I0 parts by weight of the adduct of 40 moles of ethylene oxide and I mole of castor oil. By pouring the solution into 100,000 parts by weight of water and uniformly distributing it therein an aqueous dispersion is obtained containing 0.02% by weight of the active ingredient.

V. 20 Parts by weight of compound no. 2.1 is well mixed with 3 parts by weight of the sodium salt of diisobutylnaphthalene-alpha-sulfonic acid. 17 Parts by weight of the sodium salt of a lignin-sulfonic acid obtained from a sulfite waste liquor, and 60 parts by weight of powdered silica gel, and triturated in a hammer mill. By finely distributing the mixture in 20.000 parts by weight of water, a spray liquor is obtained containing 0.1% by weight of the active ingredient.

VI. 3 parts by weight of compound no. 2.2 is intimately mixed with 97 parts by weight of particulate kaolin. A dust is obtained containing 3% by weight of the active ingredient.

VII. 30 parts by weight of compound no. 2.g is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.12 is intimately mixed with 2 parts of the calcium salt of dodecylbenzenesulfonic acid, 8 parts of a fatty alcohol polyglycol ether. 2 parts of the sodium salt of a phenolsulfonic acid-urea-formaldehyde condensate and 68 parts of a paraffinic mineral oil. A stable oily dispersion is obtained.

IX. 90 parts by weight of compound no. 3.1 is mixed with 10 parts by weight of N-methyl-alpha-pyrrolidone. A mixture is obtained which is suitable for application in the form of very fine drops.

X. 20 parts by weight of compound no. 1.3 is dissolved in a mixture consisting of 80 parts by weight of xylene, 10 parts by weight of the adduct of 8 to 10 moles of ethylene oxide and 1 mole of oleic acid-N-monoethanolamide. 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XI. 20 parts by weight of compound no. 3.4 is dissolved in a mixture consisting of 40 parts by weight of cyclohexenone, 30 parts by weight of isobutanol. 20 parts by weight of the adduct of 7 moles of ethylene oxide and 1 mole of isooctylphenol, and 10 parts by weight of the adduct of 40 moles of ethylene oxide and I mole of castor oil. By pouring the solution into 100,000 parts by weight of water and finely distributing it therein, an aqueous dispersion is obtained containing 0.02% by weight of the active ingredient.

XII. 20 parts by weight of compound no. 1.1 is dissolved in a mixture consisting of Z5 parts by weight of cyclohexenone, 65 parts by weight of a mineral oil fraction having a boiling point between 210 and 280° C. and 10 parts by weight of the adduct of 40 moles of ethylene oxide and 1 mole of castor oil. By pouring the solution into 100,000 parts by weight of water and uniformly distributing it therein an aqueous dispersion is obtained containing 0.02% by weight of the active ingredient.

XIII. 20 parts by weight of compound no. 1.1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By finely distributing the mixture in 20.000 parts by weight of water a spray liquor is obtained containing 0.1% by weight of the active ingredient.

XIV. 3 parts by weight of compound no. 1.3 is intimately mixed with 97 parts by weight of particulate kaolin. A dust is obtained containing 3% by weight of the active ingredient.

XV. 30 parts by weight of compound no. 2.7 is intimately mixed with a mixture consisting of 92 parts by weight of Powdered silica gel and 8 parts by weight of paraffin oil which has been sprayed onto the surface of this silica gel. A formulation of the active ingredient is obtained having good adherence.

XVI. 20 parts by weight of compound no. 3.3 is intimately mixed with 2 parts of the calcium salt of dodecylbenzenesulfonic acid, 8 parts of a fatty alcohol polyglycol ether. 2 parts of the sodium salt of a phenolsulfonic acid-urea-formaldehyde condensate and 68 parts of a paraffinic mineral oil. A stable oily dispersion is obtained.

The active ingredients or the herbicidal or growth-regulating agents containing them may be applied pre- or postemergence. If certain crop plants tolerate the active ingredients less well, or if the plants are to continue to grow uninfluenced application techniques may be used in which the herbicidal agents are sprayed from suitable equipment in such a manner that the leaves of sensitive crop plants are if possible not touched, and the agents reach the soil or the unwanted plants growing beneath the crop plants post-directed, lay-by treatment.

when the active ingredients are used as herbicides, the application rates depend on the objective to be achieved, the time of the year, the plants to be combated and their growth stage and are from 0.001 to 3, preferably 0.01 to 2, kg of active ingredient per hectare.

The compounds of the formula I may exercise a variety of influences on practically all plant development stages, and are therefore used as growth regulators. The diversity of action of growth regulators depends especially on
 a the type and variety of plant;
 b) the time applied, with reference to the development stage of the plants and the time of the year;
 c) the place and method of application seed treatment, soil treatment, or application to foliage;
 d) climatic factors, e.g., average temperature, amount of precipitation, sunshine and duration;
 e) soil conditions including fertilization;
 f) the formulation of the active ingredient; and
 g) the concentration at which the active ingredient is applied.

A description of some of the various possibilities of using the growth regulators of the formula I according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks. sportsgrounds, fruit orchards, lawns and airfields, thus reducing expensive and time-consuming mowing.

A further feature of economic interest is the increase in the rigor of crops which tend to lodge, such as cereals, indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

In fruit and other trees, pruning costs can be reduced with growth regulators, with growth regulators, it is also possible to break up the alternate breeding rhythm of fruit trees.

Growth regulators may also increase or inhibit lateral branching. This is of interest when, for instance in tobacco plants, it is desired to inhibit the formation of lateral shoots suckers in favor of leaf development.

With growth regulators, it is possible for instance in winter rape to considerably increase the resistance to freeze injury. On the one hand, upward growth and the development of a too luxuriant and thus particularly frost-susceptible leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase, in other crops, too. e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various especially fungus diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom leaves, fruit, seed grains, roots and tubers, to increase the sugar content of sugarbeets, sugarcane and citrus fruit to raise the protein content of cereals and soybeans, and to stimulate the increased formation of latex in rubber trees.

The compounds of the formula 1 may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening abscission of the adherence of stalks to the branches of citrus fruit, olive trees, and other kinds of pomes, drupes and indehiscent fruit. The same mechanism, i.e. promotion of the formation of separation layers between fruit or leaf and stem of the plant, is also essential for a readily controllable defoliation of crop plants, e.g.. cotton.

D. Further, transpiration in crop plants may be reduced with growth regulators. This is particularly important for Plants growing in agricultural areas which are expensive to irrigate. e.g.. in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

E. with growth regulators of the formula 1 it is also possible to restrict the growth of unwanted plants. In this way, the competition of weeds and weed grasses with field crops can be reduced without there being any direct herbicidal action. It is also possible for instance in fruit and grapes, to reduce to a considerable extent the competition of undergrowth to the advantage of the crop plants without destroying the grasses or weeds. This provides a closed soil cover and thus for example better biological activity in the soil and protection against erosion.

The growth regulators of the formula 1 according to the invention may be applied not only to the seed as a dressing, but also to the soil. i.e., via the roots, and—the method particularly preferred—to the foliage by spraying.

As a result of the good tolerance by crop plants, the application rate may vary within wide limits.

In view of the number of application methods possible, the compounds according to the invention, or agents containing them, may be used in a large number of crops for removing unwanted plants and for regulating plant growth.

To increase the spectrum of action and to achieve synergistic effects, the compounds laccording to the invention may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2.6-dinitroanilines, N-phenylcarbamates thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero-aryloxyphenoxypropionic acids and salts, esters, amides thereof, etc.

It may also be useful to apply the compounds 1, either alone or in combination with other herbicides, in admixture with other crop protection agents. e.g., agents for combating pests or phytopathogenic fungi or bactera.

Examples of further growth regulators area certain quaternary ammonium compounds, triazolyls, imidazoles, norbornanodiazetines, 4-pyridines, ethephon, abscisic acid and structures derived therefrom.

The compounds may also be mixed with solutions of mineral salts used to remedy nutritional or trace element deficiencies. Non-phytotoxic oils and oil concentrates may also be added.

Use examples

The herbicidal action of the cyclohexenone compounds 1 according to the invention is demonstrated in greenhouse experiments:

The vessels employed were plastic flowerpots having a volume of 300 $cm^3$ and filled with a sandy loam containing about 3.0% humus. The seeds of the test plants were sown separately, according to species.

For the preemergence treatment, the active ingredients, suspended or emulsified in water, were applied through finely distributing nozzles to the surface of the soil immediately after the seeds had been sown. After the agents had been applied the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment the plants were grown, depending on growth form, to a height of 3 to 15 cm before being treated with the compounds, suspended or emulsified in water. The application rate for postemergence treatment was 0.25 kg/ha.

The pots were set up in the greenhouse, heat-loving species at 20 to 35° C, and species from moderate climates at 10 to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants employed were Avena fatua Echinochloa crus-galli. Lolium multlflorum. Medicago sativa and Setaria italica.

Unwanted grassy plants were combated very well by the compound of Example 2.4 applied postemergence at a rate of 0.25 kg/ha. Alfalfa, a broadleaved crop plant, suffered no damage whatsoever.

In view of the spectrum of weeds which can be combated, the tolerance of the active ingredients by crop plants, or the desired influence of the growth thereof, and in view of numerous application methods possible, the cyclohexenone derivatives of the formula 1 may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |

-continued

| Botanical name | Common name |
| --- | --- |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. *vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To determine the growth-regulating properties of the candidate compounds, a culture medium was supplied with sufficient nutrients, and test plants were grown therein in plastic pots approx. 12.5 cm in diameter and having a volume of about 500 ml.

In the preemergence treatment, the test substances were poured onto the seed bed as aqueous formulations on the day of sowing.

In the postemergence treatment, the candidate compounds were applied to the plants as aqueous formulations. The growth-regulating action observed was confirmed at the end of the experiment by measuring the growth height. The Figures obtained were compared with those for untreated plants. 2-Chloroethyltrimethylammonium chloride (CCC) was used for comparison purposes.

Not only was growth height reduced—the leaves also took on a more intense color. The increased chlorophyll content is indicative of a higher rate of photosynthesis, making for bigger yields.

The individual data are given in the following tables; the concentration is given in mg of active ingredient per vessel (a.i./vessel).

TABLE 1

Spring wheat, "Ralle" variety
Preemergence treatment

| Example no. | Concentration mg a.i./vessel | Relative growth height |
| --- | --- | --- |
| untreated | — | 100 |
| CCC | 6 | 70.8 |
| 1.2 | 6 | 54.9 |

TABLE 2

Spring wheat, "Ralle" variety
Postemergence (leaf) treatment

| Example no. | Concentration mg a.i./vessel | Relative growth height |
| --- | --- | --- |
| untreated | — | 100 |
| CCC | 6 | 83.0 |
| 1.2 | 6 | 64.3 |

TABLE 3

Spring barley, "Aramir" variety
Preemergence treatment

| Example no. | Concentration mg a.i./vessel | Relative growth height |
| --- | --- | --- |
| untreated | — | 100 |
| CCC | 6 | 78.8 |
| 1.2 | 6 | 60.6 |

TABLE 4

Spring barley, "Aramir" variety
Postemergence (leaf) treatment

| Example no. | Concentration mg a.i./vessel | Relative growth height |
| --- | --- | --- |
| untreated | — | 100 |
| CCC | 6 | 91.6 |
| 1.2 | 6 | 58.5 |

TABLE 5

Rice, "Bahia" variety
Postemergence (soil) treatment

| Example no. | Concentration mg a.i./vessel | Relative growth height |
| --- | --- | --- |
| untreated | — | 100 |
| CCC | 1.5 | 100.0 |
| | 6 | 99.6 |
| 1.2 | 1.5 | 56.9 |
| | 6 | 40.9 |
| 1.3 | 1.5 | 69.3 |
| | 6 | 46.2 |
| 3.1 | 1.5 | 94.2 |
| | 6 | 92.5 |
| 3.2 | 1.5 | 96.0 |
| | 6 | 90.7 |
| 3.3 | 1.5 | 94.2 |
| | 6 | 81.8 |
| 3.4 | 1.5 | 100.0 |
| | 6 | 88.9 |

TABLE 6

Rice, "Bahia" variety
Postemergence (leaf) treatment

| Example no. | Concentration mg a.i./vessel | Relative growth height |
|---|---|---|
| untreated | — | 100 |
| CCC | 1.5 | 98.1 |
| 1.2 | 1.5 | 53.5 |
| 1.3 | 1.5 | 53.5 |
| 3.1 | 1.5 | 72.9 |
| 3.2 | 1.5 | 74.4 |
| 3.3 | 1.5 | 68.4 |
| 3.4 | 1.5 | 66.9 |

TABLE 7

Sunflowers, "Spanners Allzweck" variety
Postemergence (leaf) treatment

| Example no. | Concentration mg a.i./vessel | Relative growth height |
|---|---|---|
| untreated | — | 100 |
| CCC | 1.5 | 89.2 |
| 1.2 | 1.5 | 73.9 |
| 1.3 | 1.5 | 72.5 |

TABLE 8

Spring rape, "Petranova" variety
Postemergence (leaf) treatment

| Example no. | Concentration mg a.i./vessel | Relative growth height |
|---|---|---|
| untreated | — | 100 |
| CCC | 1.5 | 95.9 |
| 1.2 | 1.5 | 70.2 |
| 1.3 | 1.5 | 83.9 |
| 3.1 | 1.5 | 82.2 |
| 3.2 | 1.5 | 82.2 |
| 3.3 | 1.5 | 78.8 |
| 3.4 | 1.5 | 83.9 |

We claim:

1. A cyclohexenone of the formula

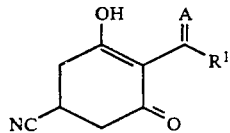

where the substituents have the following meanings:
$R^1$ is
(a) $C_1-C_{20}$-alkyl, $C_2-C_{20}$-alkenyl,
$C_2-C_{20}$-alkynyl or
$C_3-C_6$-cycloalkyl, each of which is unsubstituted or bears one or more halogen substituents,
(b) $C_2-C_6$-alkoxyalkyl,
(c) $C_2-C_6$-alkylthiealkyl, or
(d) benzyl or phenyl,
each of the aromatic nuclei being unsubstituted or bearing from one to three halogen, cyano, $C_1-C_4$-alkyl, $C_1-C_4$-alkoxy, $C_1-C_4$-haloalkyl or nitro substituents;
A is $NOR^2$ where:
$R^2$ is $C_1-C_4$-alkyl, $C_3-C_4$-alkenyl or $C_3-C_4$-alkynyl, each of which is unsubstituted or bears one or more substituents selected from the group consisting of halogen, $C_1-C_4$-alkoxy, and phenylradicals being unsubstituted or bearing from one to three halogen, $C_1-C_4$-alkyl, $C_1-C_4$-alkoxy, $C_1-C_4$-haloalkyl or nitro substituents; or their agriculturally utilizable salts.

2. A cyclohexane compound as et forth in claim 1, where $R^1$ and $R^2$ have the following meanings:
$R^1$ is methyl, ethyl, n-propyl, n-butyl or cyclopropyl,
$R^2$ is ethyl, allyl, (E)-but-2-en-1-yl, propargyl, but-2-yn-1-yl,
(E)-3-chloroprop-2-en-1-yl, 5-(4-fluorophenyl)-but-3-en-1-yl, 4-(4-chlorophenyl)-but-3-eny-1-yl or 5-chlorothenyl.

3. A herbicidal composition containing a herbicidally effective amount of at least one cyclohexenone compound as set forth in claim 1, and inert additives.

4. A process for combating the growth of unwanted plants, wherein the plants and/or the area to be kept free from unwanted plant growth are treated with a herbicidally effective amount of a cyclohexenone compound as set forth in claim 1.

5. A cyclohexenone compound of the formula:

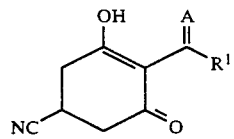

where the substituents have the following meanings:
$R^1$ is
(a) $C_1-C_{20}$-alkyl, $C_2-C_{20}$-alkenyl,
$C_2-C_{20}$-alkynyl or
$C_3-C_6$-cycloalkyl, each of which is unsubstituted or bears one or more halogen substituents,
(b) $C_2-C_6$-alkoxyalkyl,
(c) $C_2-C_6$-alkylthioalkyl, or
(d) benzyl or phenyl,
each of the aromatic nuclei being unsubstituted or bearing from one to three halogen, cyano, $C_1-C_4$-alkyl, $C_1-C_4$-alkoxy, $C_1-C_4$-haloalkyl or nitro substituents;
A is oxygen or $NR^3$, where:
$R^3$ is hydrogen, $C_1-C_6$-alkyl,
$C_1-C_4$-hydroxyalkyl,
$C_2-C_4$-alkoxyalkyl,
$C_2-C_4$-alkylthioalkyl, phenyl, or benzyl, the last two radicals being unsubstituted or bearing from one to three halogen, $C_1-C_4$-alkyl, $C_1-C_4$-alkoxy, $C_1-C_4$-haloalkylornitro substituents;
or their agriculturally utilizable salts.

6. A cyclohexenone compound as set forth in claim 5, where substituents $R^1$ and $R^3$ have the following meanings:
$r^1$ is methyl, ethyl, n-propyl, n-butyl or cyclopropyl,
$R^3$ is hydrogen, methyl, ethyl, n-propyl, isopropyl, n-butyl, s-butyl, isobutyl, n-hexyl, allyl, 2-methoxyethyl, benzyl or phenyl.

7. A composition for regulating plant growth, containing a plant growth regulating effective amount of a cyclohexenone compound as set forth in claim 5, and inert additives.

8. A process for regulating the growth of plants, wherein a bioregulatory amount of a cyclohexenone compound as set forth in claim 5 is applied to plants and/or their habitat.

* * * * *

UNITED STATES PATENT AND TRADEMARK OFFICE
CERTIFICATE OF CORRECTION

PATENT NO. : 5,085,689

DATED : Feb. 4, 1992

INVENTOR(S) : KAST et al.

It is certified that error appears in the above-identified patent and that said Letters Patent is hereby corrected as shown below:

On the title page: Item [75],

The first name of the sixth named inventor should read "Wilhelm"

Claim 1, column 19, line 55, delete "alkythiealkyl"

and insert ---alkylthioalkyl--.

Claim 2, column 20, line 3, delete "cyclohexane" and insert

--cyclohexone--;

column 20, line 3, delete "et" and insert --set--;

column 20, line 8, delete "5-(4-fluorophenyl)- and insert --4-(4-fluorophenyl)---.

column 20, line 9, delete "4-(4-chlorophenyl)- but-3-eny-1-yl" and insert --4-(4-chlorophenyl)-but-2-en- 1-yl, 4-(4-fluorophenyl)-but-3-en-1-yl, 4-(4-chlorophenyl)- but-3-en-1-yl--.

Claim 5, column 20, line 47, delete "$C_1$-$C_4$-haloalkylornitro"

UNITED STATES PATENT AND TRADEMARK OFFICE
CERTIFICATE OF CORRECTION

PATENT NO. : 5,085,689  
DATED : Feb. 4, 1992  
INVENTOR(S) : KAST et al.

PAGE 2 of 2

It is certified that error appears in the above-identified patent and that said Letters Patent is hereby corrected as shown below:

and insert --$C_1$-$C_4$-haloalkyl or nitro--.

Claim 6, column 20, line 52, delete "$r^1$" and insert --$R^1$--.

Signed and Sealed this

Twenty-seventh Day of April, 1993

Attest:

MICHAEL K. KIRK

*Attesting Officer*  Acting Commissioner of Patents and Trademarks